(12) United States Patent
Rolfe

(10) Patent No.: US 6,699,220 B2
(45) Date of Patent: Mar. 2, 2004

(54) INJECTOR PACK

(75) Inventor: Steven Mark Guy Rolfe, Oxford (GB)

(73) Assignee: Owen Mumford Limited, Oxford (GB)

(*) Notice: Subject to any disclaimer, the term of this patent is extended or adjusted under 35 U.S.C. 154(b) by 0 days.

(21) Appl. No.: 10/009,502

(22) PCT Filed: Apr. 10, 2001

(86) PCT No.: PCT/GB01/01645
§ 371 (c)(1),
(2), (4) Date: Dec. 11, 2001

(87) PCT Pub. No.: WO01/76666
PCT Pub. Date: Oct. 18, 2001

(65) Prior Publication Data
US 2002/0161339 A1 Oct. 31, 2002

(30) Foreign Application Priority Data
Apr. 12, 2000 (GB) .............................. 0008955

(51) Int. Cl.⁷ ................................................. A61M 5/20
(52) U.S. Cl. ...................................................... 604/136
(58) Field of Search ................................ 604/131, 136, 604/130, 137, 191, 204

(56) References Cited

U.S. PATENT DOCUMENTS 4,329,988 A * 5/1982 Sarnoff et al. .............. 128/218
4,578,064 A * 3/1986 Sarnoff et al. .............. 604/191
5,137,516 A 8/1992 Rand et al.

FOREIGN PATENT DOCUMENTS

WO    WO 99/06100    2/1999

* cited by examiner

Primary Examiner—Sharon Kennedy
(74) Attorney, Agent, or Firm—Young & Thompson

(57) ABSTRACT

An injector pack has a box which houses in separate positions a firing mechanism and a syringe housing. The firing mechanism has safe and cocked conditions and as it is located in the box it is constrained to adopt the safe condition by a sleeve grip being held against rotation while a protruding barrel co-operates with cams to rotate it. The firing mechanism when removed can be screwed by its barrel to the rear end of the syringe housing while that is held by the box, and then the whole injector can be withdrawn for use. The syringe is made operable by rotating the barrel to the cocked condition. Pressing the grip forwards then releases a plunger to act on the syringe. The previous retraction of the plunger can be done using a pillar formation upstanding within the box and over which the barrel can be sleeved.

13 Claims, 4 Drawing Sheets

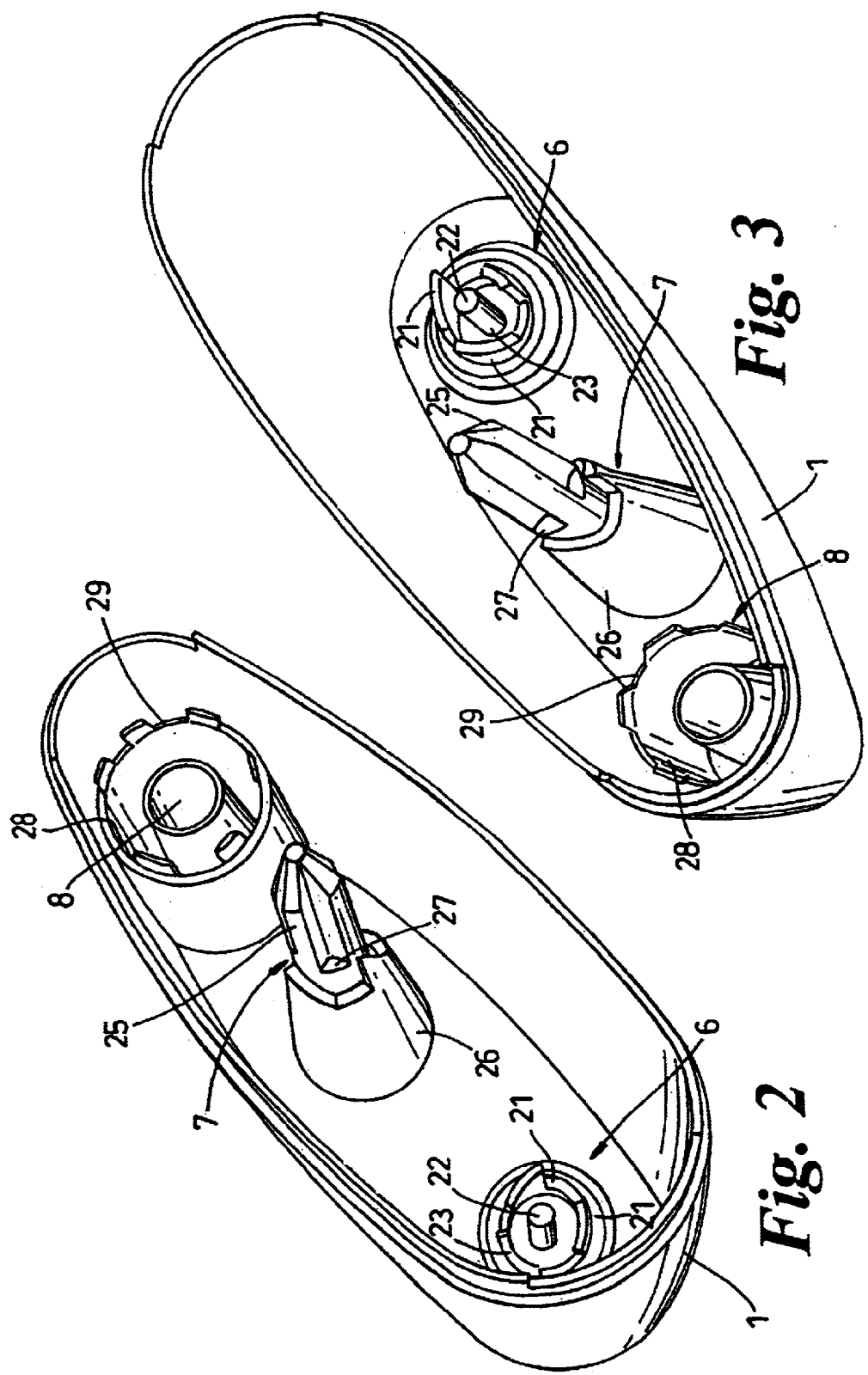

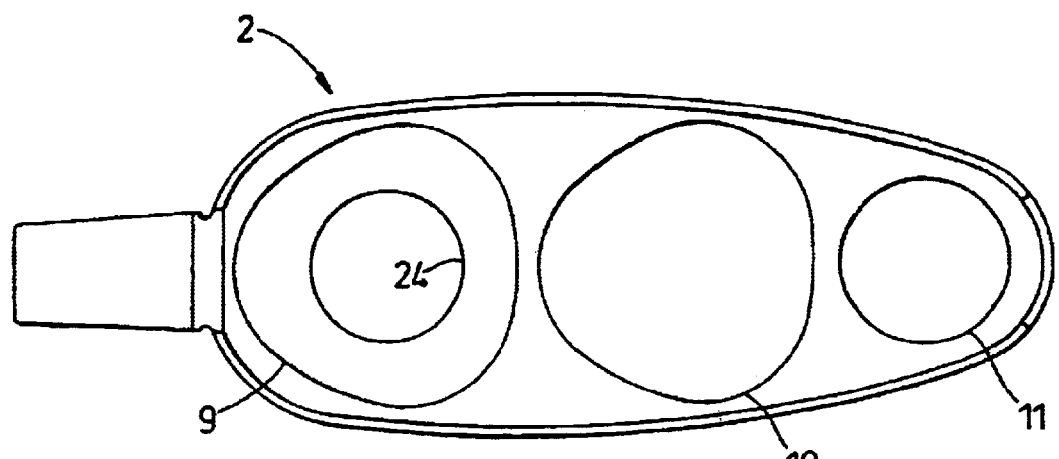
Fig. 6
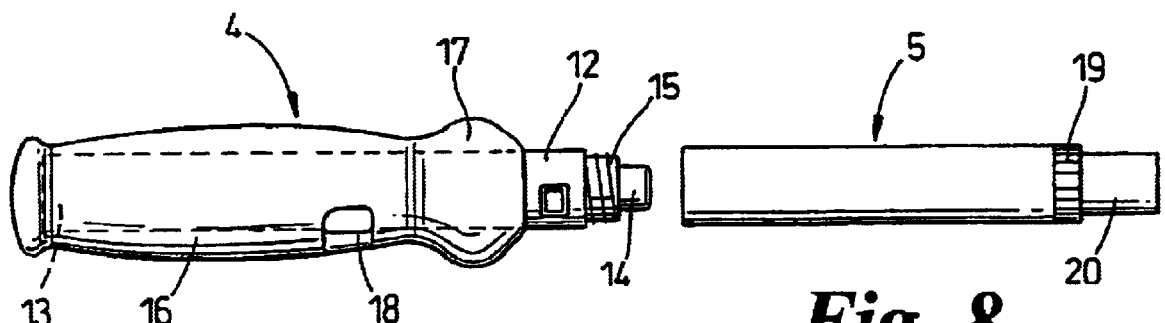
Fig. 7
Fig. 8
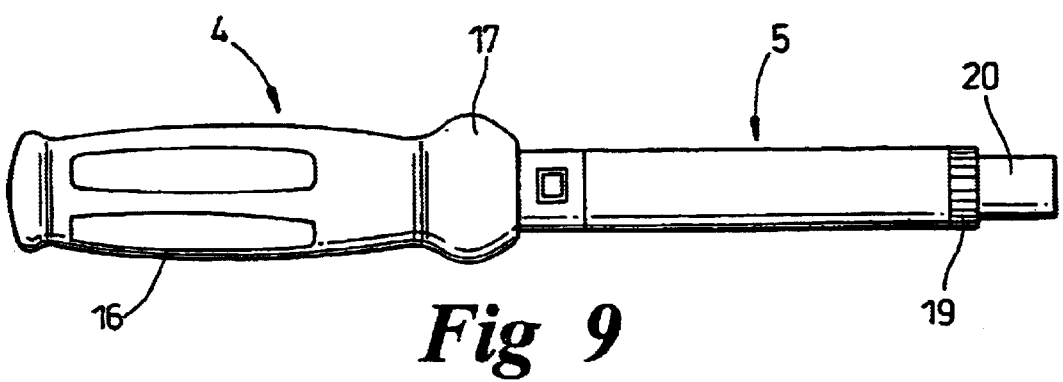
Fig 9

INJECTOR PACK

BACKGROUND OF THE INVENTION

This invention concerns an injector pack.

DESCRIPTION OF THE RELATED ART

It is common for sufferers from arthritis to give themselves injections, but often they have difficulty, by virtue of their condition, in handling and using syringes.

SUMMARY OF THE INVENTION

It is the aim of this invention to provide a pack containing an injection device stored in a safe and disassembled condition, but which can easily be assembled, cocked and fired, even by those with impaired manual dexterity.

According to the present invention there is provided an injector pack comprising a box, a syringe housing, and a firing mechanism attachable to the housing and having an actuator to release a plunger from a retracted position to propel a syringe within the housing to project its needle from the housing and then to express a dose through the needle, wherein the box has internal structure which constrains the actuator into a safe condition when the firing mechanism is in a stowed position therein, and which stows the syringe housing separately to present its rear end for the attachment of the firing mechanism when that is removed from its stowed position, the syringe housing being removable from the box by the attached firing mechanism and the actuator being adjustable when the firing mechanism is free of the box to a cocked condition where it can be manipulated to release the plunger.

Conveniently, with the plunger retracted, the actuator will be rotatable between the safe condition and the cocked condition. This rotation may also be carried out with the plunger released or fired.

In the preferred form, the firing mechanism has a barrel from the forward end of which the plunger emerges, and the actuator is tubular, sleeved over the barrel (so that it can serve as a grip), and with a closed rear end which forms part of the plunger release. The barrel can have a seat in a lower part of the box and the actuator a seat in the box above the barrel seat. These seats can be non-circular and in a relationship to ensure that the relative rotational positions of the barrel and actuator put the actuator in the safe condition.

The actuator seat may be a regular, substantially polygonal socket to receive a complementary formation on the actuator symmetrical about the axis of the barrel. The barrel seat may include an annular array of cams for engagement by a complementary array of cams around the barrel at its leading end. The engagement of the cams then causes or confirms rotation of the barrel to a position where the actuator is in the safe condition.

Conveniently, the plunger is tubular, at least at its leading end. A pin upstanding within the box can then enter the plunger and guide it, and thus the firing mechanism, as that mechanism is stowed in the box.

It is desirable for the actuator to be in its safe condition before the plunger can be held in its retracted position. In other words, if the mechanism has been fired, it cannot be re-cocked simply by pressing back the plunger; there also has to be mutual rotation between the actuator and the barrel.

The box can have an internal pillar, separate from the stowed positions of the syringe housing and the firing mechanism for assisting retraction of the plunger, the tip of the pillar being engageable by the leading end of the plunger when that is offered up in alignment, while the leading portion of the firing mechanism can be telescoped down over the pillar, the plunger thereby being pushed backwards.

Additionally, the pillar may have an annular array of cams around its base similar to those of the barrel seat, and the box may have an actuator guide in registry with the pillar. This can ensure that, as the barrel is sleeved over the pillar and the plunger reaches its fully retracted position, the relative rotational positions of the barrel and the actuator are such that the actuator is in its safe condition.

Preferably the syringe housing will be held against rotation when stowed in the box. If the firing mechanism screw couples to the housing, as is preferred, holding the box holds the housing fast while the firing mechanism is rotated. This turning of the firing mechanism to tighten the screw coupling should be in the same direction as rotating the actuator from the cocked to the safe condition.

The leading end of the syringe housing will preferably have a needle cover, lightly sprung, normally to project beyond the housing and shroud the needle after use. The needle itself will generally have a rubber cap for further protection and hygiene, and in the lower part of the box that locates the housing there can be a formation of known type to strip off the cap when the housing is removed.

Preferably, there will be a window in the grip, and a mark or sign on the barrel which will register with this window when the firing mechanism is safe. Another mark or sign may show when it is cocked.

BRIEF DESCRIPTION OF THE DRAWINGS

For a better understanding of the invention, one embodiment will now be described, by way of example, with reference to the accompanying drawings, in which:

FIG. 2 is a perspective view looking down into the box without a lining member,

FIG. 3 is another perspective view looking down into the box without the lining member, FIG. 6 is a plan view of the lining member, FIG. 7 is a side view of a firing mechanism forming part of the injector device, FIG. 8 is a side view of a syringe holder forming part of the injector device, and FIG. 9 is a side view of the firing mechanism and syringe housing assembled together.

DESCRIPTION OF THE PREFERRED EMBODIMENTS

Figure 1:
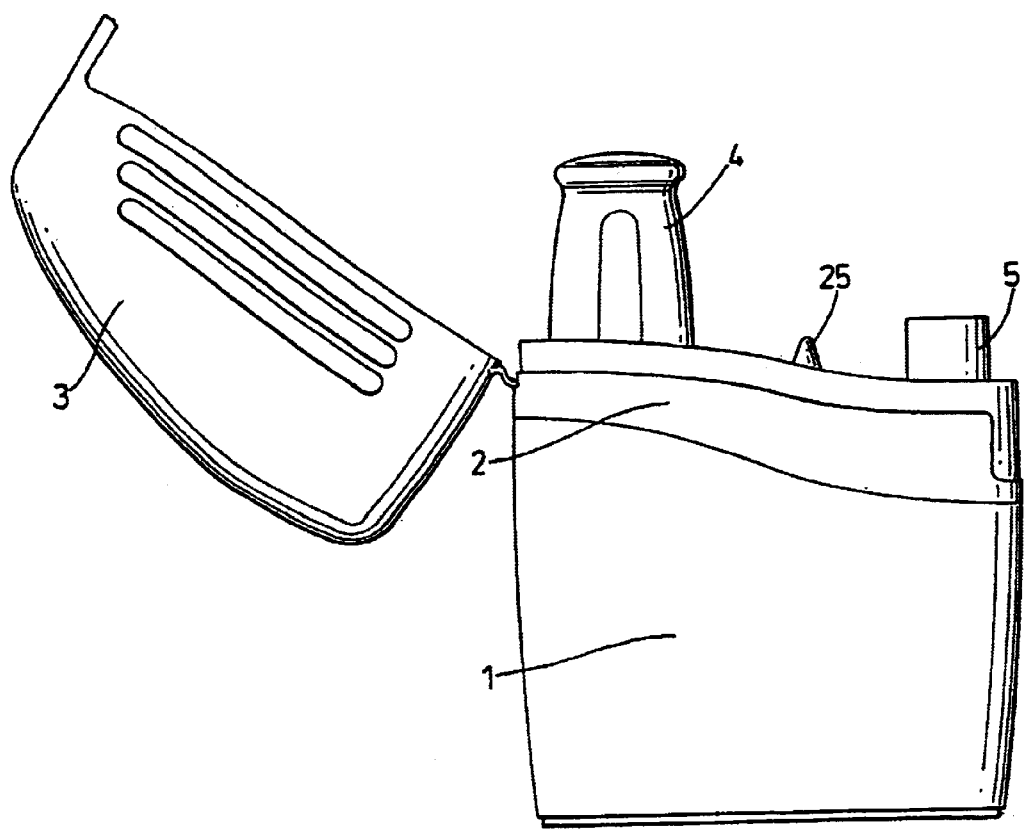
FIG. 1 is a side view of a box containing a disassembled injector device.
Figure 4:
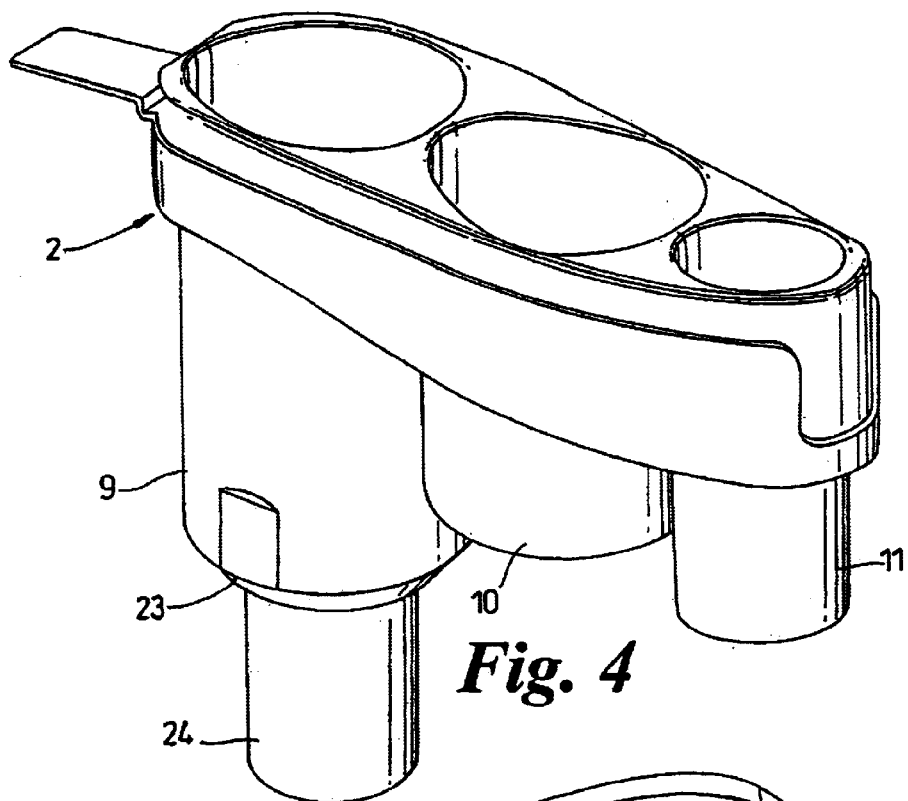
FIG. 4 is a perspective view from above of the lining member.
Figure 5:
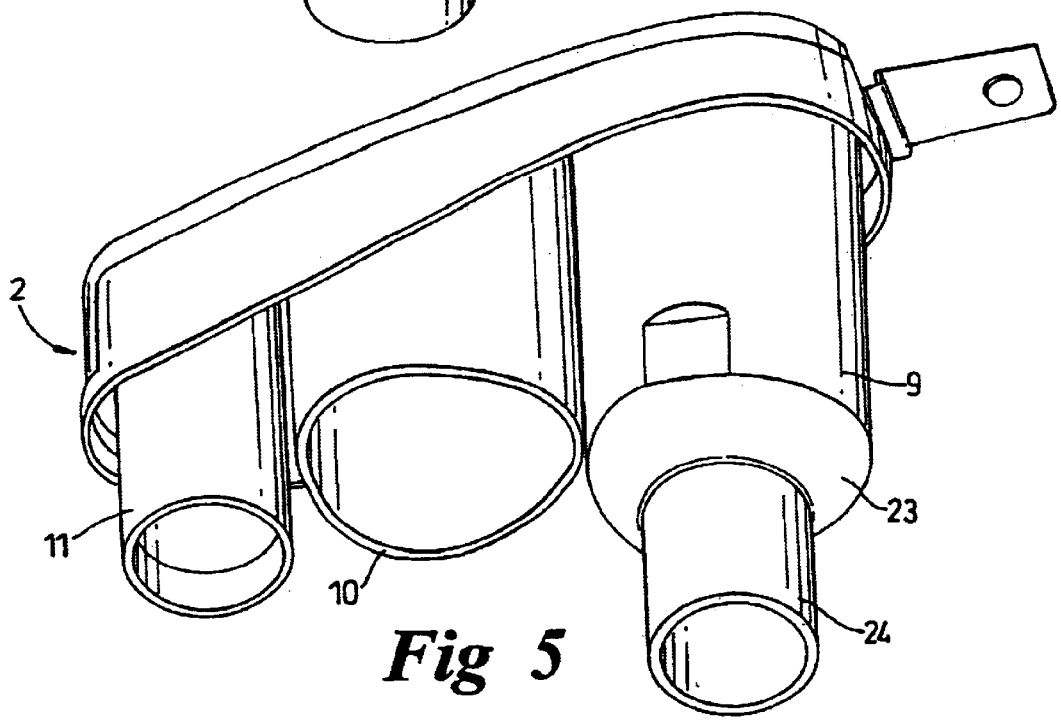
FIG. 5 is a perspective view from below of the lining member.

The main components of the pack are a box 1, an inner lining/guide member 2 for the box, a lid 3 hinged to the box 1 via the member 2, a firing mechanism 4, and a syringe housing 5.

The box 1 has three internal formations 6, 7 and 8 in alignment along its base. The formation 6 locates the leading end of the firing mechanism 4 and ensures that it will be in the locked or safe condition when properly stowed in the box. The formation 7 is used to cock the firing mechanism, and the formation 8 locates the leading end of the syringe housing 5. All these will be described in more detail below.

The member 2 provides guides 9 and 10 for the firing mechanism, to ensure that it registers properly with the formations 6 and 7, and a guide 11 for the syringe housing to align that properly with the formation 8. Again, these will be described in more detail below.

The firing mechanism 4 has a barrel 12 at the rear end of which is a knob 13. This is pressed to release a drive spring (not shown) which shoots forward a plunger 14 from the leading end of the barrel. It emerges from a reduced screw threaded portion 15 by which a connection is made to the syringe housing 5. But the knob 13 can only be so pressed when in a cocked condition, and this is achieved by rotating the barrel 12 from a safety condition relative to a surrounding sleeve 16. The actual knob 13 itself is not accessible; it is concealed by the closed rear end of this sleeve 16, which extends forwardly over the barrel, terminating externally in a rounded triangular formation 17 just short of the portion 15. The rest of the sleeve may be a body of rotation, and it serves as a grip for the user. It has a window 18 through which a mark or marks on the barrel 12 may be seen.

The syringe housing 5 is mostly a straight cylinder, internally threaded at its rear end to engage the portion 15 and having a shallow toothed annulus 19 at its leading end from which normally projects a lightly sprung needle shroud 20. The syringe itself is not shown.

The formation 6 is a set of three triangular teeth 21 in an annular array around a stud 22. The teeth have curved, sloping faces 23 all facing in the same circumferential direction, and following similar helical paths. They form cams which co-operate with complementary formations (not shown) inside the portion 15 of the barrel 12. They do not of course obstruct the plunger 14. With the sleeve grip 16 held against rotation and in any of three orientations about its axis, as the firing mechanism is pushed down on to the formation 6, these cam surfaces rotate the barrel 12 relative to the sleeve 16 so that the barrel is in the safe position and the knob 13 inoperable. The stud 22 enters the hollow leading end of the plunger 14 to assist location, if that plunger is in its fired, forward position. But stowage with the plunger retracted is also possible.

The upper part of the guide 9 of the member 2 is also of rounded triangular cross-section to match the portion 17 so that, as the firing mechanism 4 is entered, the sleeve 16 is constrained into one of those three orientations and prevented from rotation. The guide 9 narrows at a shoulder 23 into a short cylindrical section 24 which closely receives the leading end of the barrel 12.

For use, the firing mechanism 4 is removed from this storage location and, if the plunger has been fired, offered up to the formation 7. This has a pillar 25 of cruciform cross-section with a tapered and rounded top. It is upstanding from a frusto-conical base 26 and around its lower end there is a set of teeth 27 similar to the teeth 21. As the firing mechanism is pushed down on to the pillar 25, that engages the plunger 14 and presses it back into the barrel 12. As the portion 15 reaches the teeth 27 these ensure that the barrel 12 is rotated relative to the sleeve 16 so that the plunger is caught in its retracted position with the drive spring fully compressed. This can only happen if the barrel 12 is in the safe condition. It should be, the firing mechanism having just been removed from the formation 6, but in case it has somehow been re-adjusted the teeth 27 perform the same function as the teeth 21 and restore the firing mechanism to the safe condition.

The guide 10 of the member 2 is a short cylinder of rounded triangular cross-section which acts in the same way as the upper part of the guide 9 to keep the sleeve 16 in the correct orientation by virtue of the complementary formation 17.

The firing mechanism is then lifted off the pillar 25 and offered up to the syringe housing 5 which is located at its forward end by the formation 8 and at an intermediate position by the guide 11 of the member 2. The formation 8 has a cup 28 with recesses 29 to match and receive the teeth of the annulus 19, and thereby prevent rotation of the housing 5. Within the cup there is a boot remover to co-operate with a rubber cap over the needle of the syringe. The user can simply screw the portion 15 into the rear end of the housing 5, press down on the assembly to engage the boot remover with the rubber cap, and then lift the assembly free. This screw action will not accidentally cause the firing-mechanism to revert to the cocked condition; it will if anything accentuate the rotation into the safe condition.

As the assembly is lifted clear, the boot remover will retain hold of the cap and expose the needle, although that will at that point be safely within the housing 5. The needle shroud 20 which will have been pushed back into the housing 5 in the stowed position, will spring out on removal of the assembly.

The injection device is now almost ready to use. All it needs is a relative twist between the sleeve 16 and the exposed part of the barrel 12 to put it into the cocked position. The friction of the screw engagement should allow the housing 5 to be held and turned relative to the sleeve, if that proves more convenient. The condition can be checked by observing marks or signs on the barrel 12 through the window 18.

The device is then applied to the user's skin with light pressure to cause the shroud 20 to retract. The sleeve 16 is pushed forward, and the knob 13 causes the plunger to fire. After use, as the needle is extracted, the shroud 20 moves forward to protect it.

What is claimed is:

1. An injection pack comprising a box, a syringe housing, and a firing mechanism attachable to the housing and having an actuator to release a plunger from a retracted position to propel a syringe within the housing to project its needle from the housing and then to express a dose through the needle, wherein the box has internal structure which constrains the actuator into a safe condition when the firing mechanism is in a stowed position therein, and which stows the syringe housing separately to present its rear end for the attachment of the firing mechanism when that is removed from its stowed position, the syringe housing being removable from the box by the attached firing mechanism and the actuator being adjustable when the firing mechanism is free of the box to a cocked condition where it can be manipulated to release the plunger, and wherein at least with the plunger retracted, the actuator is rotatable between the safe condition and the cocked condition.

2. An injection pack as claimed in claim 1, wherein the syringe housing is held against rotation when stowed in the box, and wherein the firing mechanism screw couples to the housing.

3. An injection pack as claimed in claim 1, wherein the firing mechanism has a barrel from the forward end of which the plunger emerges, and the actuator is tubular, sleeved over the barrel, and with a closed rear end which forms part of the plunger release.

4. An injection pack as claimed in claim 3, wherein the barrel has a seat in a lower part of the box and the actuator has a seat in the box above the barrel seat which seats are non-circular and in a relationship to ensure that the relative rotational positions of the barrel and actuator put the actuator in the safe condition.

5. An injection pack as claimed in claim 4, wherein the actuator seat is a regular, substantially polygonal socket to receive a complementary formation on the actuator symmetrical about the axis of the barrel.

6. An injection pack as claimed in claim 4, wherein the barrel seat includes an annular array of cams for engagement by a complementary array of cams around the barrel at its leading end, the engagement of the cams causing or confirming rotation of the barrel to a position where the actuator is in the safe condition.

7. An injection pack as claimed in claim 1, wherein the plunger is tubular, at least at its leading end, and wherein a pin is upstanding within the box, the pin entering the plunger and guiding it, and thus the firing mechanism, as that mechanism is stowed in the box.

8. An injection pack as claimed in claim 1, wherein the actuator has to be in its safe condition before the plunger can be held in its retreated position.

9. An injection pack as claimed in claim 6, wherein the box has an internal pillar separate from the stowed positions of the syringe housing and the firing mechanism, for assisting retraction of the plunger, the tip of the pillar being engageable by the leading end of the plunger when that is offered up in alignment, while the leading portion of the firing mechanism can be telescoped down over the pillar, the plunger thereby being pushed backwards.

10. An injection pack as claimed in claim 9, wherein the pillar has an annular array of cams around its base similar to those of the barrel seat, and the box has an actuator guide in registry with the pillar thereby ensuring that, as the barrel is sleeved over the pillar and the plunger reaches its fully retracted position, the relative rotational positions of the barrel and the actuator are such that the actuator is in its safe condition.

11. An injection pack as claimed in claim 1, wherein the syringe housing is held against rotation when stowed in the box, and wherein the firing mechanism screw couples to the housing.

12. An injection pack as claimed in claim 11, wherein the turning of the firing mechanism to tighten the screw coupling is in the same direction as rotating the actuator from the cocked to the safe condition.

13. An injection pack as claimed in claim 1, wherein the box has an internal pillar separate from the stowed positions of the syringe housing and the firing mechanism, for assisting retraction of the plunger, the tip of the pillar being engageable by the leading end of the plunger when that is offered up in alignment, while the leading portion of the firing mechanism can be telescoped down over the pillar, the plunger thereby being pushed backwards.

* * * * *